US011661606B2

(12) United States Patent
Landry et al.

(10) Patent No.: US 11,661,606 B2
(45) Date of Patent: May 30, 2023

(54) MATURE PLANT TRANSFECTION USING CARBON NANOTUBES

(71) Applicant: The Regents of the University of California, Oakland, CA (US)

(72) Inventors: Markita P. Del Carpio Landry, Berkeley, CA (US); Gozde Sultan Demirer, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/672,459

(22) Filed: Nov. 2, 2019

(65) Prior Publication Data

US 2020/0063148 A1   Feb. 27, 2020

Related U.S. Application Data

(63) Continuation of application No. PCT/US2018/030563, filed on May 2, 2018.

(60) Provisional application No. 62/500,450, filed on May 2, 2017.

(51) Int. Cl.
*C12N 15/82* (2006.01)

(52) U.S. Cl.
CPC ..... *C12N 15/8206* (2013.01); *C12N 15/8218* (2013.01)

(58) Field of Classification Search
CPC ............ C12N 15/8206; C12N 15/8207; C12N 15/8201
See application file for complete search history.

(56) References Cited

U.S. PATENT DOCUMENTS

2013/0185823 A1 * 7/2013 Kuang ............... C12N 15/8202
800/278

OTHER PUBLICATIONS

Burlaka, O.M., Pirko, Y.V., Yemets, A.I. et al. Plant genetic transformation using carbon nanotubes for DNA delivery. Cytol. Genet. 49, 349-357 (2015). https://doi.org/10.3103/S009545271506002X.*
Kato, Yuichi & Niidome, Takuro & Nakashima, Naotoshi. (2011). Thermodynamics of the Exchange of Solubilizers on Single-walled Carbon Nanotubes. Chemistry Letters. 40. 730. 10.1246/cl.2011.730.*
Liu, Y., Wu, D.-C., Zhang, W.-D., Jiang, X., He, C.-B., Chung, T.S., Goh, S.H. and Leong, K.W. (2005), Polyethylenimine-Grafted Multiwalled Carbon Nanotubes for Secure Noncovalent Immobilization and Efficient Delivery of DNA. Angewandte Chemie International Edition, 44: 4782-4785. doi:10.1002/anie.200500042.*
Maged F. Serag, Noritada Kaji, Enrica Venturelli, Yukihiro Okamoto, Kazuyoshi Terasaka, Manabu Tokeshi, Hajime Mizukami, Kevin Braeckmans, Alberto Bianco, and Yoshinobu Baba. (2011), Functional Platform for Controlled Subcellular Distribution of Carbon Nanotubes. ACS Nano 5 (11), 9264-9270. DOI: 10.1021/nn2035654.*
Bridget D. Dolash, Roya R. Lahiji, Dmitry Y. Zemlyanov, Vladimir P. Drachev, Ronald Reifenberger, Donald E. Bergstrom, Sonication mediated covalent cross-linking of DNA to single-walled carbon nanotubes, Chemical Physics, vol. 413, 2013, pp. 11-19, ISSN 0301-0104, https://doi.org/10.1016/j.chemphys.2012.07.00.*
Nham Tran, Mitch Raponi, Ian W. Dawes, Greg M. Arndt, Control of specific gene expression in mammalian cells by co-expression of long complementary RNAs, FEBS Letters, vol. 573, Issues 1-3, 2004, pp. 127-134, ISSN 0014-5793, https://doi.org/10.1016/j.febslet.2004.07.075.*
Slater, S.M.H., Keller, W.A. & Scoles, G. Agrobacterium-mediated transformation of Eruca sativa. Plant Cell Tiss Organ Cult 106, 253-260 (2011). https://doi.org/10.1007/s11240-010-9915-1.*
Vasil, V., Castillo, A., Fromm, M. et al. Herbicide Resistant Fertile Transgenic Wheat Plants Obtained by Microprojectile Bombardment of Regenerable Embryogenic Callus. Nat Biotechnol 10, 667-674 (1992). https://doi.org/10.1038/nbt0692-667.*
Lörz, H., Baker, B. & Schell, J. Gene transfer to cereal cells mediated by protoplast transformation. Molec Gen Genet 199, 178-182 (1985). https://doi.org/10.1007/BF00330256.*
Umemura K. (2015). Hybrids of Nucleic Acids and Carbon Nanotubes for Nanobiotechnology. Nanomaterials (Basel, Switzerland), 5(1), 321-350. https://doi.org/10.3390/nano5010321.*
Zhuang Liu, Mark Winters, Mark Holodniy, and Hongjie Dai, siRNA Delivery into Human T Cells and Primary Cells with CarbonNanotube Transporters, 2007, Angewandte chemie, 119, 2069-2073 (Year: 2007).*
Azadeh Hashem Nia and Mohammad Ramezani, Evaluation of chemical modification effects on DNA plasmid transfection efficiency of singlewalled carbon nanotube-succinate-polyethylenimine conjugates as non-viral gene carriers, Nov. 30, 2016, The royal society of chemistry, 2017, 8, 364 (Year: 2016).*
Tom Clemente, Nicotiana (Nicotiana tobaccum, Nicotiana benthamiana), 2006, Agrobacterium Protocols Second Edition vol. 1, pp. 143-154 (Year: 2006).*
Transient Transfection, ThermoFisher Scientific, https://www.thermofisher.com/us/en/home/references/gibco-cell-culture-basics/transfection-basics/transfection-methods/transient-transfection.html (Year: 2021).*
Hellens, Transient expression vectors for functional genomics, quantification of promoter activity and RNA silencing in plants, Plant Methods, Dec. 18, 2005 (Year: 2005).*
Jones, Transient transformation of Plants, Methods in Molecular Biology, Plant Genomics, vol. 513, 2009 (Year: 2009).*

(Continued)

*Primary Examiner* — Matthew R Keogh
*Assistant Examiner* — Brian James Sullivan
(74) *Attorney, Agent, or Firm* — Richard Aron Osman (57) ABSTRACT

Nano-sized delivery vehicles utilize carbon nanotubes (CNTs) for the generic, targeted and passive transport of biomolecules into plant cells. Plant cells are transfected by adsorbing a charged biomolecular cargo on carbon nanotubes by electrostatic grafting or by dialysis-based pi-pi stacking grafting or by probe-tip sonication of complementary nucleic acid strands; and introducing into the cell the cargo-adsorbed nanotubes.

2 Claims, 7 Drawing Sheets

(56) References Cited

OTHER PUBLICATIONS

Steinberg, Physiology of the Tobacco Plant, 1958, Annual Reviews of Plant Physiology, Issue 9, pp. 151-174 (Year: 1958).*
Bashandy, Within leaf variation is the largest source of variation in agroinfiltration of Nicotiana benthamiana, Plant Methods, 2015, 11:47 (Year: 2015).*
Sparkes, Rapid, Transient expression of fluorescent fusion proteins in tobacco plants and generation of stably transformed plants, Nature, Nov. 30, 2006, vol. 1 No. 4 (Year: 2006).*
Liu, Preparation of fluorescence starch-nanoparticle and its application as plant transgenic vehicle, Journal of Central South University, 2008 (Year: 2008).*
Smith, Stable vs. Transient Transfection of Eukaryotic Cells, Biocompare Life Science Articles, Jan. 3, 2013 (Year: 2013).*
Gallego, A Deep Overview of Stable and Transient Transformation, GOLDBIO, Accessed 2022 (Year: 2022).*
Ying, Transient Expression of Transferred Gene Induced by Polyethylenimine, Scientia Agricultura Sinica, 2009 (Year: 2009).*

\* cited by examiner

MATURE PLANT TRANSFECTION USING CARBON NANOTUBES

INTRODUCTION

Plant bioengineering has a wide variety of impactful applications and has experienced exciting progress since the production of the first transgenic plants. However, current methods of biomolecule delivery to mature plants are limited due to the presence of plant cell wall, and are additionally hampered by low transfection efficiency, high toxicity of the transfection material, and host range limitation[1]. Therefore, in most cases, transfection is limited to protoplast cultures where the cell wall is removed, and not to the mature whole plant. However, protoplasts from most plant species are not able to regenerate into fertile plants, causing these methods to have low practical applicability[2]. Given these limitations of conventional gene delivery methods to mature plants, the plant genome engineering community can benefit from a delivery method that is inexpensive, facile, and robust, and that can transfer biomolecules into all phenotypes of any plant species with high efficiency and low toxicity.

It was previously shown that certain high-aspect-ratio nanomaterial formulations can penetrate the mature plant cell and also the chloroplast, and deliver single-stranded DNA[3,4]. We have developed and optimized a delivery method that can transfer biomolecules into both model and crop plant species, and both monocot (wheat) and dicot (arugula, Nicotiana benthamiana) plant species with high efficiency and no toxicity, using modified single-walled and multi-walled carbon nanotubes (CNTs) for efficient through-cell-wall delivery into mature plant cells in a passive and species-independent manner[5].

Relevant literature includes: Karmakar et al. International J Nanomedicine 2011:6 1045-1055; the inventors presented limited, non-enabling disclosures in Gozde S. Demirer, Markita P. Landry, Delivering Genes to Plants, SBE Special Section, Plant Synthetic Biology, CEP Magazine, April 2017, and the 2016 AIChE Annual Meeting, the International Conference on Plant Synthetic Biology and Bioengineering (ICPSBB) in December 2016, the 2017 AIChE Annual Meeting, and the 2018 BPS Annual Meeting.

SUMMARY OF THE INVENTION

The invention provides methods and compositions for loading, adsorbing or grafting a biomolecular cargo to, on or onto carbon nanotubes.

In an aspect, the invention provides a method of adsorbing a biomolecular cargo on carbon nanotubes comprising dialyzing a mixture of suspended, surfactant-adsorbed nanotubes and the cargo using a dialysis membrane permeable to the surfactant and impermeable to the cargo and nanotubes, wherein the surfactant desorbs from the nanotubes and the cargo adsorbs onto the nanotubes via ligand exchange.

In an aspect, the invention provides a dialysis system comprising a mixture of suspended, surfactant-adsorbed nanotubes and a biomolecular cargo bounded by a dialysis membrane permeable to the surfactant and impermeable to the cargo and carbon nanotubes.

In an aspect, the invention provides a method for delivering functional small interfering RNA (siRNA) molecules into plant cells through suspending carbon nanotubes with the sense and antisense strands of siRNA as two separate solutions via probe-tip sonication, and introducing an equimolar mixture of these solutions into plant cells.

In an aspect, the invention provides a method of transfecting a plant cell comprising: adsorbing a charged biomolecular cargo on charged carbon nanotubes by electrostatic grafting, or by dialysis-based pi-pi stacking grafting, or by probe-tip sonication based pi-pi stacking grafting; and introducing into the cell the cargo-adsorbed nanotubes, e.g. by positively charging the surface of carbon nanotubes through chemical reaction to attach negatively charged nucleic acids via electrostatic attraction.

In embodiments, the cargo is a nucleic acid, a protein, a nucleoprotein such as a ribonucleoprotein (RNP), or a drug, and particularly wherein the cargo is a nucleic acid that is ssDNA, dsDNA, ssRNA, dsRNA, siRNA or ds hybrid DNA/RNA, particularly large, protein-encoding dsDNA vectors.

In the embodiments, plant cells are of true mature leaves of *Eruca sativa* (arugula), *Triticum aestivum* (wheat), *Nicotiana benthamiana* (wild type and mGFP5 mutant); mesophyll protoplast cells extracted from the true mature leaves of *Eruca sativa* (arugula), *Triticum aestivum* (wheat), or *Nicotiana benthamiana* (wild type and mGFP5 mutant).

In embodiments of dialysis-mediated ligand exchange:
  the method further comprises the antecedent step of adsorbing the surfactant (sodium dodecyl sulfate-SDS) onto pristine carbon nanotubes to form the surfactant-adsorbed nanotubes;
  the dialysis membrane has a pore size that allows exit/passage of desorbed surfactant but not of the cargo nor nanotubes;
  the method further comprises the subsequent step of transfecting cells (bacterial, animal, plant) with the cargo-adsorbed nanotubes; and/or In embodiments of dual probe-tip sonication mediated siRNA adsorption step:
  the method further comprises the antecedent step of adsorbing each strand of siRNA onto pristine single-walled carbon nanotubes separately via probe-tip sonication;
  the method further comprises mixing of equimolar carbon nanotube suspensions of each strand, followed by immediate subsequent step of transfecting cells (bacterial, animal, plant) with the cargo-adsorbed nanotubes; and/or In embodiments of electrostatic grafting the adsorbing step:
  the carbon nanotubes are functionalized with polyethylenimine (PEI), and/or
  the method further comprises the antecedent step of reacting carboxylated carbon nanotubes with polyethylenimine (PEI) to form functionalized PEI functionalized carbon nanotubes.

The method generally provides for directly adsorbing molecular cargos to the nanotubes via charge-charge interactions. The method provides for charge-based attraction of the cargos to the nanotubes.

The invention enables delivery of molecules, including double-stranded plasmids, or double-stranded large linearized DNA vectors, particularly encoding functional proteins. The method also can deliver small interfering RNA molecules.

Applications of the invention include: agriculture, e.g. to improve yield and profitability, to delay ripening of fruits, to create crops that are resistant to drought, insects, herbicides and diseases, and/or higher potential for clean bioenergy production; the pharmaceutical industry and in medicine, e.g. to synthesize novel small-molecule drugs, mass-produce drugs, human growth hormones, antibodies, and vaccines;

research and development, e.g. to determine functions of genes, and in the energy industry, e.g. more efficient and clean biofuels, improved biofuel production, and better waste conversion to alcohol and fuel.

The invention encompasses all combinations of the particular embodiments recited herein, as if each combination had been laboriously recited.

DESCRIPTION OF PARTICULAR EMBODIMENTS OF THE INVENTION

Unless contraindicated or noted otherwise, in these descriptions and throughout this specification, the terms "a"

and "an" mean one or more, the term "or" means and/or and polypeptide sequences are understood to encompass opposite strands as well as alternative backbones described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

We disclose a nano-sized delivery vehicle that utilizes carbon nanotubes (CNTs) for the generic, targeted and passive transport of biomolecules into cells, and particularly of mature plants of any plant species for wide variety of applications.

CNTs are made by rolling graphene sheets into cylindrical and hollow nanostructures that are nanometers in diameter and micrometers in length. Depending on how many graphene sheets are used during production, CNTs can be single-walled (SWCNT) or multi-walled (MWCNT). Pristine (non-modified) CNTs are not soluble in aqueous solutions owing to their hydrophobicity, and hence, they must be modified before used in any biological system. Our invention includes the surface modification of SWCNTs and MWCNTs through covalent and non-covalent processes to render water solubility, and to conjugate DNA and RNA onto CNT surfaces for transient transformation of mature plants. No alternatives currently exist to conjugate double-stranded DNA onto CNTs, or to conjugate functional double-stranded siRNA molecules for use in plant systems. One of the distinct advantages of our method is that the same mechanisms of modification and conjugation can be used to bind different biomolecules onto the surface of CNTs, hence, for diverse applications.

Some of the general utilities and related applications of our CNT-based delivery vehicles are:

Delivery of plasmid DNA and double-stranded linearized DNA vectors into mature plant cell nucleus: In agriculture, this approach can be employed for transformation of plants to create crops that are resistant to herbicides, insects, diseases, and drought. Additionally, the ability to introduce transgenes into plant cells also provides the opportunity to improve the nutrient profile of a crop. In the pharmaceutical industry, delivery of genetic material through CNTs can be used to synthesize valuable small-molecule drugs by plants. Additionally, CNT-based delivery vehicles have great potential to improve biofuel production from plants through genetic modification.

Delivery of plasmid DNA and double-stranded linearized DNA vectors into mature plant organelles: Plastids are double-lipid membrane plant organelles with their own circular double-stranded DNA, known as plastome. In plants, plastids differentiate into several forms (chloroplast, elaioplast, amylopast, proteinoplast, etc.) depending on their function in the cell, and they are the site of manufacture and storage of vital compounds produced and consumed by the cell. Therefore, genetic engineering of plastomes may have wide range of applications, such as photosynthesis energy upconversion in the case of chloroplast DNA engineering, and increased biofuel production in the case of elaioplast (fat storage) or amylopast (starch storage) DNA engineering.

Delivery of RNA into mature plant cell cytosol: Our modified CNT vehicles can be conjugated to small interfering RNA (siRNA) to achieve short term gene silencing or knockdown in mature plants. siRNA is the most commonly used RNA interference (RNAi) tool in plants. However, like gene delivery, current methods of siRNA delivery to plants are also hindered by cell death, low efficiency, limited host range, etc. Our CNT-based vehicles can effectively deliver siRNA into plant cytosol for several applications, such as investigating the individual contributions of genes to a variety of cellular events, identifying novel pathways, and selectively targeting and suppressing the disease-causing genes in mature plants. Additionally, our vehicles can be utilized to deliver guide RNA (gRNA) to mature plants for gRNA-directed RNA or DNA editing purposes Delivery of single-stranded DNA (ssDNA) sequences that are complimentary to the transcription factors in mature plants: By delivering ssDNA sequences that are complimentary to plant transcription factors, desired protein-coding gene knockouts can be achieved in mature plants. In this case, same applications with siRNA delivery are possible, by the annealing of in vivo transcription factors to the complimentary sequences on CNTs, hence not being able to activate specific gene expression.

Our CNT-based delivery vehicle offers distinct advantages over alternatives such as biolistic particle delivery, electroporation, PEG-mediated delivery and *Agrobacterium* mediated delivery, including: Plant species-independent internalization; Passive penetration of lipid bilayer membranes and cell wall; Ability to deliver cargo into mature walled-plants additional to the protoplasts; Low cytotoxicity; Moderate to high transfection efficiency; Complete experiment time frame of a week (after having plants ready); Transient transformation that is beneficial for fast screening applications and for creating edited plants without genetically modified organism (GMO) label, Conjugation of many different types of biomolecules; Wide range of applications; High practical applicability with the current technology.

Figures 1A, 1C:
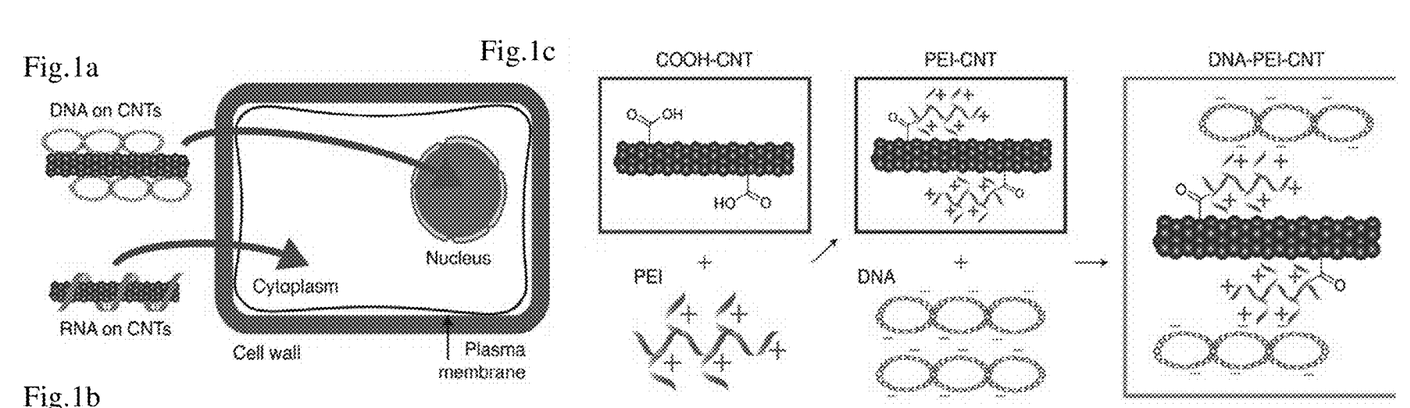
FIG. 1(a). Overarching strategy for CNT-mediated plant transformations and DNA grafting on CNTs; For expression of a functional gene, DNA is delivered into the mature plant cell nucleus with carbon nanotubes. Separately, for silencing of a functional gene, siRNA is delivered into the plant cell cytoplasm with carbon nanotubes.
FIG. 1(c) Carboxylated CNTs (COOH-CNT) are first chemically modified via covalent attachment of a cationic PEI polymer (PEI-CNT), and subsequently incubated with negatively charged DNA to form DNA loaded PEI-CNTs (DNA-PEI-CNT).

There are several ways to prepare and utilize our CNT-based delivery vehicles (FIG. 1a). First, we should note that we use both SWCNTs and MWCNTs as gene delivery tools. Even though the modification and conjugation mechanisms are exactly same for the both types of CNTs, obtained transfection efficiencies and toxicity levels are different, as CNTs differ in aspect ratio and stiffness. Here, we will explain the modification methods of CNTs to allow solubility in aqueous solutions and methods to stably conjugate plasmid DNA, double-stranded linearized DNA vectors onto modified CNT surfaces, and siRNA vectors onto pristine CNT surfaces.

Figures 6A, 6B, 6C, 6D, 6E:
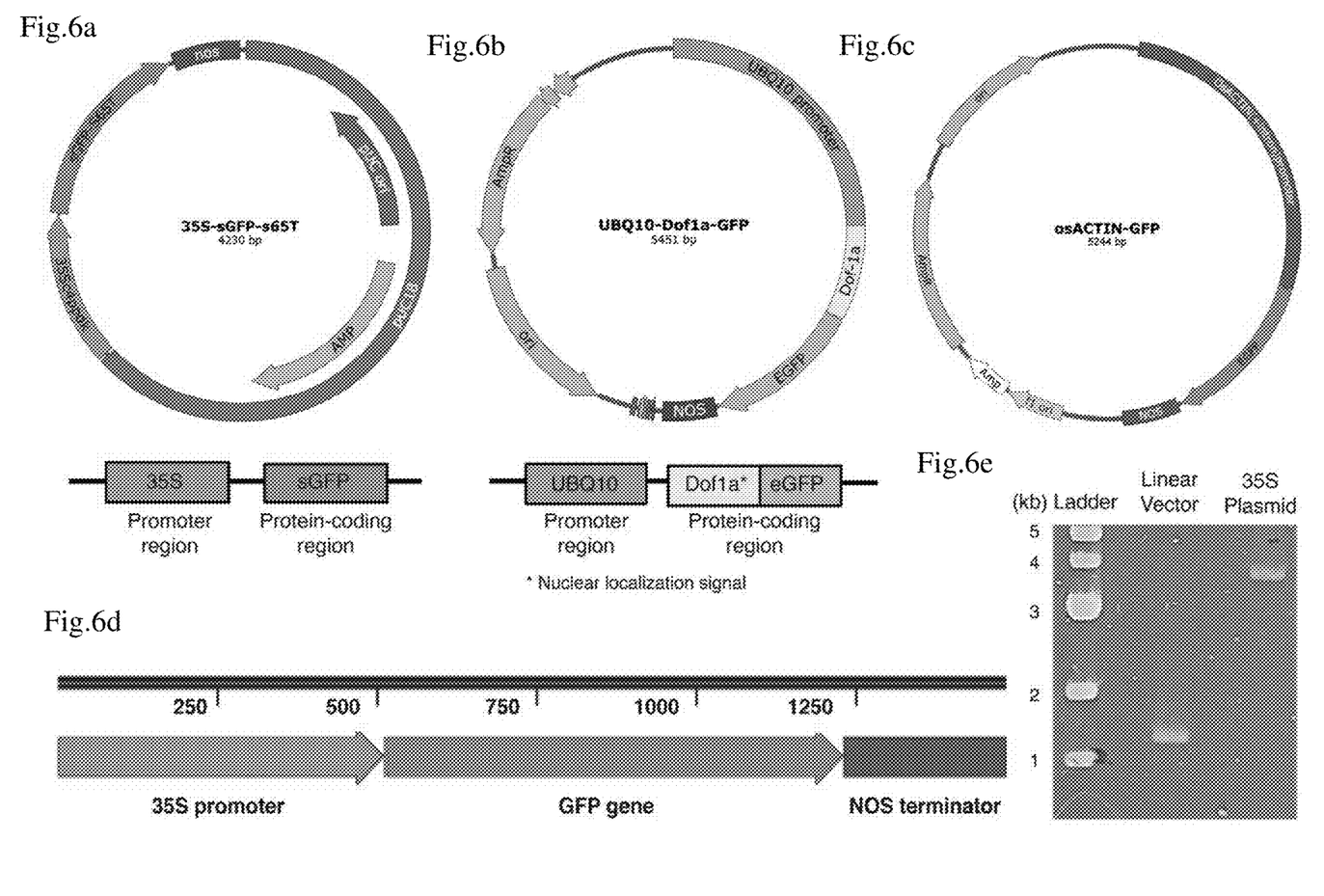
FIG. 6(a). Plasmids used in the studies and confirmation of plasmid linearization through PCR; Plasmid map for 35S dicot plasmid DNA encoding GFP that lacks a nuclear localization signal.
FIG. 6(b) Plasmid map for UBQ10 dicot plasmid DNA encoding GFP that contains a nuclear localization signal (Dof1a).
FIG. 6(c) Plasmid map for osACTIN monocot plasmid DNA encoding GFP that lacks a nuclear localization signal.
FIG. 6(d) Sanger sequencing of the linear amplicon shows error-free amplification of the promoter, GFP gene, and NOS terminator regions.
FIG. 6(e) Linearization of the 35S plasmid is accomplished through PCR amplification, and the linear amplicon that is run on a 1% agarose gel via electrophoresis shows the expected linear DNA size of 1.5 kbp.

Plasmid DNAs that we use in these experiments are generic GFP plasmids (reporters), and the plasmid maps can be seen in FIG. 6. One of the plasmids, UBQ10-DOF1a-sGFP, has a nuclear localization sequence attached to GFP, that carries all of the translated GFP from cytosol to nucleus to facilitate imaging. The other plasmids, 35sC4PPDK-sGFP and osACTIN-GFP, lacks any localization sequence, hence, the obtained GFP stays and accumulates mostly in the plant cytosol. These plasmids are also used to obtain linearized double-stranded DNA vectors through PCR. From these plasmids, promoter, GFP gene, and the terminator sequences are amplified and purified, and used in subsequent experiments of CNT adsorption and cell transfection.

Figure 1B:
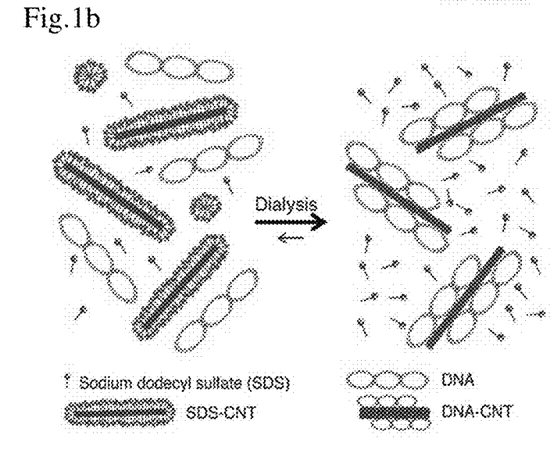
FIG. 1(b) DNA is grafted on CNTs through 7E-7E stacking, in which the initial SDS coating is gradually replaced by DNA adsorption through dialysis.

In the first method of preparation—dialysis (FIG. 1b), commercially purchased pristine SWCNTs and MWCNTs are suspended with a surfactant, sodium dodecyl sulfate (SDS) by a probe-tip sonication (70 W, 30 min). Sonicated mixture is then centrifuged (16000 g, 90 min) to remove unsuspended nanotubes, and the recovered supernatant is characterized using a UV-Vis spectrometer. SDS suspended CNTs (SDS-CNTs), produced by this simple and easily scalable process, are water soluble and can be stored at room temperature for extended time periods. Plasmid DNA and linearized DNA (both double-stranded and containing the gene of interest) conjugation to CNTs is then achieved via direct adsorption of dsDNA through a dialysis procedure. In this dialysis, ligand exchange procedure, SDS-CNTs and free dsDNA are placed into an accurately-pore-sized dialysis cartridge (20K), that will allow the exit of desorbed SDS from CNT surface, while free dsDNA adsorbs to and suspends CNTs via pi-pi stacking interactions. After ~3-4 days of dialysis, by changing the dialysis buffer (0.1M NaCl) daily, we obtain a stable suspension of dsDNA conjugated CNTs (pDNA-CNTs). The preparation protocol is same for both plasmids and the linearized DNA vectors. The product is characterized by the fluorescence emission spectra of CNTs and also with an agarose gel electrophoresis. To introduce genetic material loaded carbon nanotubes to plants, *Eruca sativa* (arugula), *Triticum aestivum* (wheat) and *Nicotiana benthamiana* leaves are infiltrated with dsDNA-CNT solution using a syringe from the under-side of leaves. Infiltrated leaves are imaged with confocal microscopy for GFP expression after ~3 days (FIG. 2). As seen from confocal images, we have achieved considerable transfection efficiency by using direct adsorption method without any observed cytotoxicity.

However, due to the estimated weakness of the pi-pi interaction that holds dsDNA and CNTs together, we hypothesized that some of dsDNA may be desorbing from the surface of CNTs before reaching to nucleus, and limiting the transfection efficiency for the direct adsorption method.

Figure 1D:
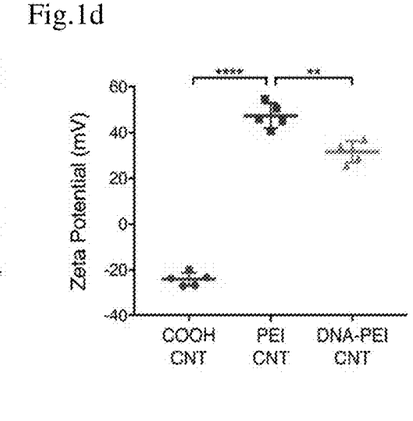
FIG. 1(d) PEI and DNA binding on CNTs is validated by zeta potential measurements: The −24.1 mV zeta potential of COOH-CNT increases to +47.4 mV after reaction with PEI, due to positively charged PEI binding, and subsequently decreases to +31.7 mV when incubated with negatively charged DNA, confirming DNA adsorption.
Figure 1E:
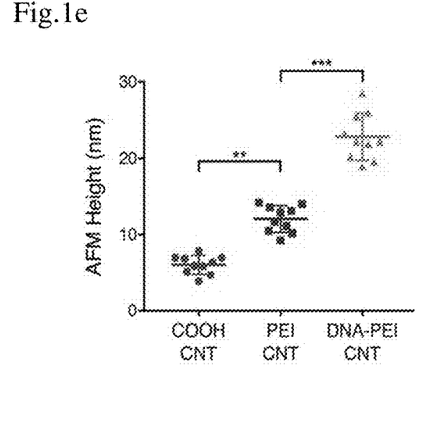
FIG. 1(e) Average height profile of CNTs is obtained through AFM imaging. Nanoparticle heights before and after reaction with PEI are measured to be 6.0 and 12.1 nm for COOH- and PEI-CNT, respectively, confirming PEI binding. CNT nanoparticle height increases from 12.1 to 22.8 nm after incubation with DNA vectors, confirming DNA grafting.
Figure 2A:
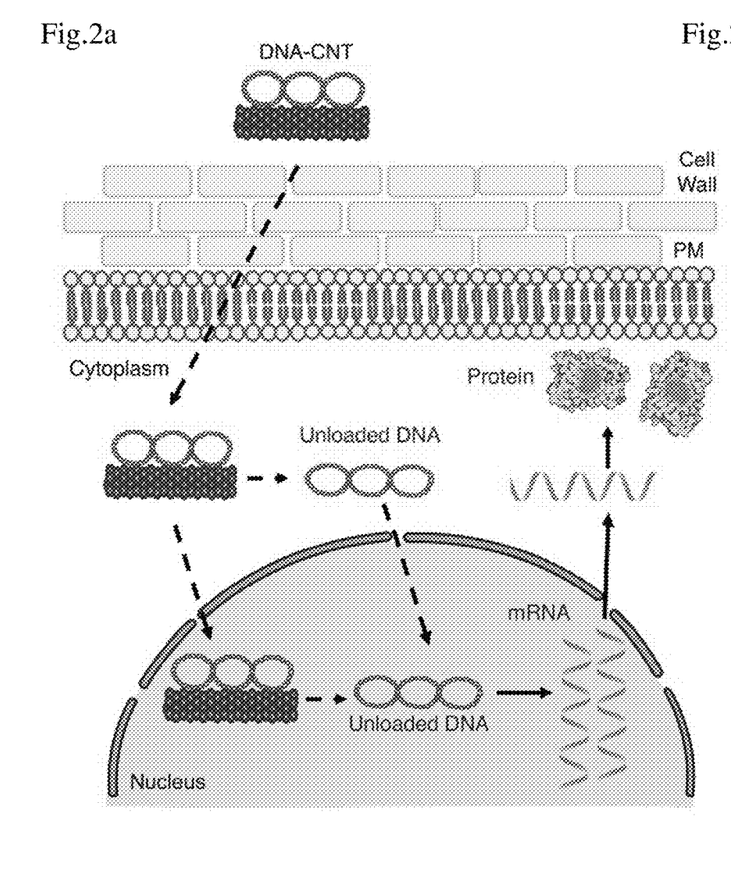
FIG. 2(a). DNA delivery into mature plants with CNTs and subsequent GFP expression; DNA-CNTs traverse the plant cell wall and membrane and enter the cytosol where DNA either desorbs in the cytosol and enters the nucleus, or DNA carried by CNTs is transported across the nuclear membrane to initiate gene expression. Dotted lines represent trafficking steps and the rigid lines represent gene expression steps.
Figure 2B:
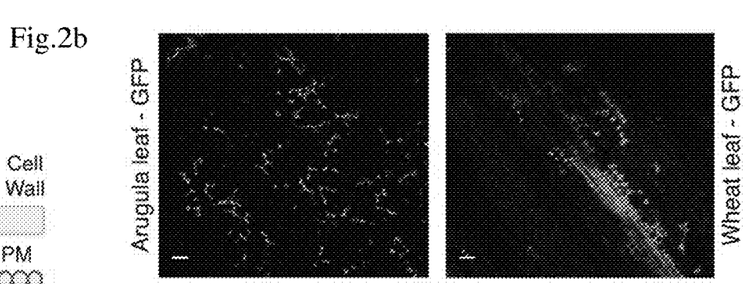
FIG. 2(b) Arugula (dicot) and wheat (monocot) leaves infiltrated with DNA-CNTs are imaged with confocal microscopy, and expression of GFP is observed in the leaf lamina. Scale bars, 50 µm.
Figure 2C:
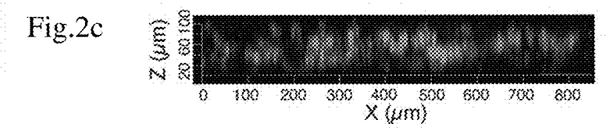
FIG. 2(c) Z-stack analysis of the fluorescence profile of the DNA-CNT treated arugula leaf shows that GFP fluorescence originates from the full thickness of the leaf, confirming that CNT nanocarriers diffuse and penetrate through the full leaf profile.
Figure 2D:
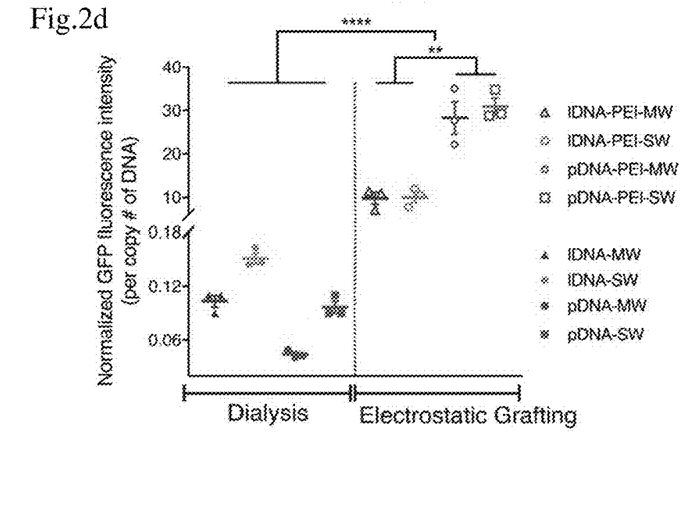
FIG. 2(d) Quantitative fluorescence intensity analysis of arugula confocal images indicates that GFP expression is significantly higher for DNA-CNTs prepared by electrostatic grafting compared to GFP expression induced by DNA-CNTs prepared via dialysis.

To increase our transfection efficiency, we developed a second method (FIG. 1c), in which we covalently modify CNT surfaces to carry a positive charge, and in this case, dsDNA conjugation (both linear dsDNA and circular plasmid dsDNA) is achieved through electrostatic grafting of DNA to the SWNT. The covalent modification reaction starts with commercially purchased carboxylated single or multi-walled CNTs (COOH-CNTs). In the presence of excess polyethylenimine (PEI) at high temperature, PEI is attached to CNTs from the carboxyl groups creating PEI-CNTs, which has a zeta potential of +50 mV after excessive washing with water to remove unreacted PEI polymer. Positively charged PEI-CNTs are then incubated with negatively charged dsDNAs (zeta potential of −60 mV) for 30 minutes, which allows for the conjugation of dsDNA onto CNTs through electrostatic attraction (FIG. 1d). After the incubation with dsDNA, zeta potential of CNTs decrease to +32 mV from +50 mV suggesting that the conjugation has occurred. The product of dsDNA-PEI-CNTs are infiltrated into *Eruca sativa, Triticum aestivum* and *Nicotiana benthamiana* leaves with the same technique (using a syringe from the under-side of leaves). Infiltrated leaves are imaged with confocal microscopy for GFP expression after ~3 days (FIG. 2b). As seen from confocal images, we have achieved a significant transfection efficiency using electrostatic grafting method.

Figure 3A:
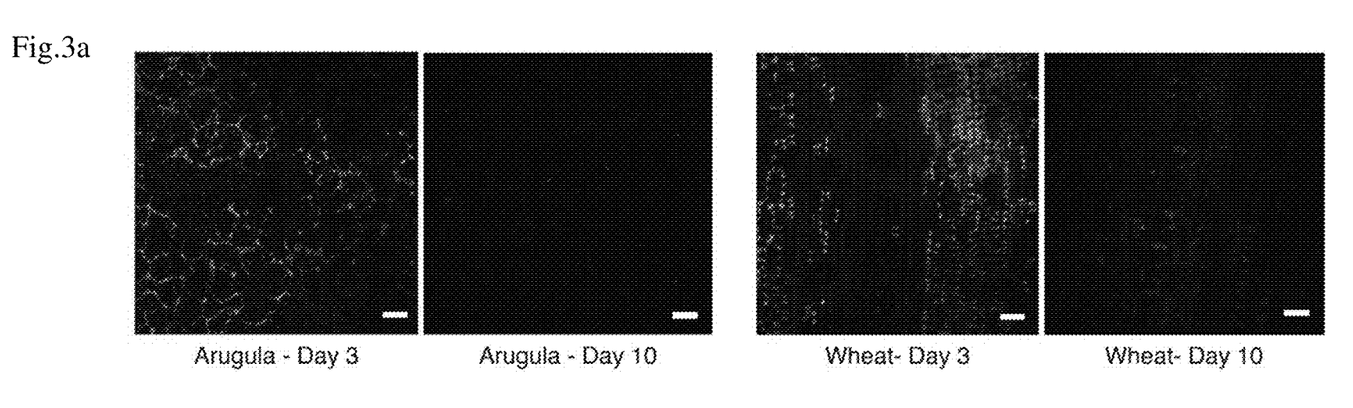
FIG. 3(a). CNT-mediated GFP expression is transient in arugula and wheat leaves; Representative confocal microscopy images showing GFP expression at Day 3 and no to minimal expression at Day 10 in DNA-CNT infiltrated mature arugula and wheat leaves. Scale bars, 50 µm FIG. 3(b) Quantitative fluorescence intensity analysis of confocal images demonstrating that GFP expression at Day 3 induced by CNT-mediated DNA delivery disappears 10-days post-infiltration.
Figure 3B:
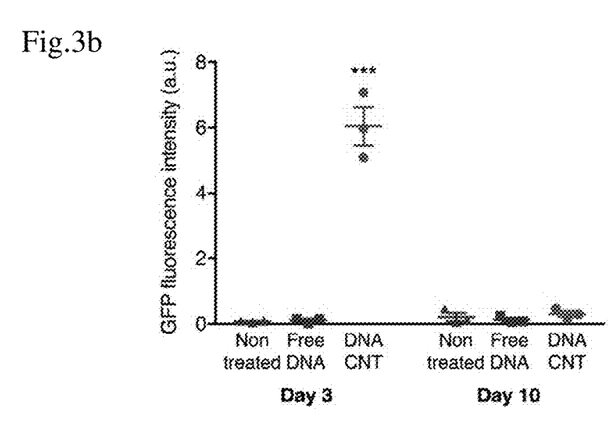
Figure 3C:
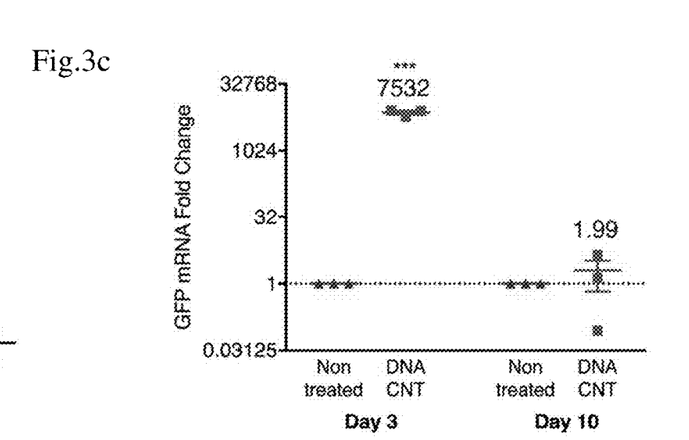
FIG. 3(c) Quantitative PCR analysis show over 7500-fold GFP mRNA change at Day 3, dropping to a 2-fold change at Day 10 in DNA-CNT treated arugula leaves compared to the non-treated leaves.

Independent of the nanomaterial formulation or plant species, we further demonstrate that CNT-mediated gene expression is transient in mature plant leaves. Representative confocal images of DNA-CNT infiltrated arugula and wheat leaves (FIG. 3a) and corresponding quantitative fluorescence intensity analysis of these images demonstrate that the highest GFP fluorescence intensity at Day 3 disappears by Day 10 (FIG. 3b). Similarly, quantitative PCR (qPCR) analysis of GFP mRNA collaborates our confocal imaging results. For DNA-CNT treated arugula leaves, we observe an over 7500-fold GFP mRNA change 3-days post-infiltration, which drops to an insignificant two-fold mRNA change by Day 10 in DNA-CNT treated arugula leaves, as compared to non-treated arugula leaves (FIG. 3c). Our results both at the mRNA transcript and fluorescent protein expression levels demonstrate that GFP expression is transient and suggest that genes delivered into plant cells via CNT carriers do not integrate into the plant nuclear genome.

Figure 4A:
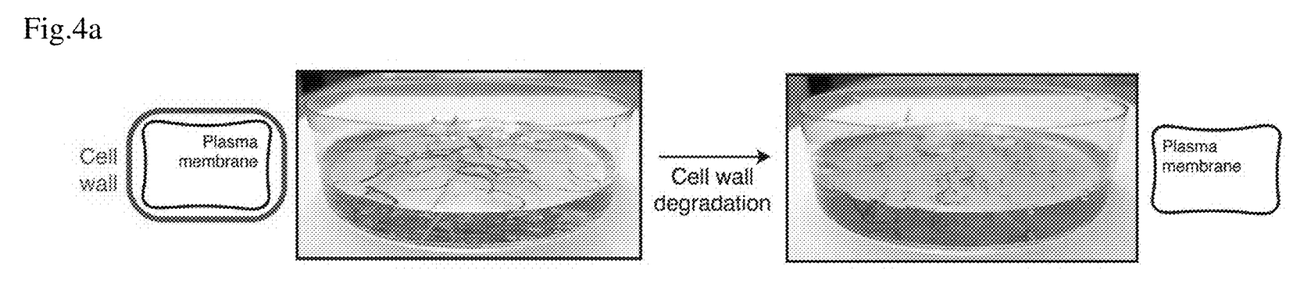
FIG. 4(a). DNA delivery into isolated protoplasts with CNTs and subsequent GFP expression; Intact and healthy protoplasts are extracted from arugula leaves through enzymatic cell wall degradation with high efficiency and high yield ($10^7$ total protoplast/10 leaves).
Figure 4B:
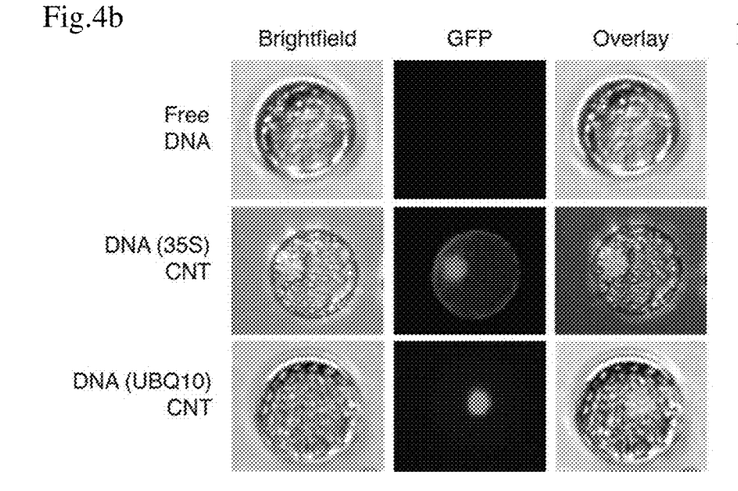
FIG. 4(b) Protoplasts incubated with 35S and UBQ10 DNA-CNTs show strong GFP expression correctly localized in cells. Protoplasts incubated with free DNA without CNT nanocarriers do not show GFP expression.
Figure 4C:
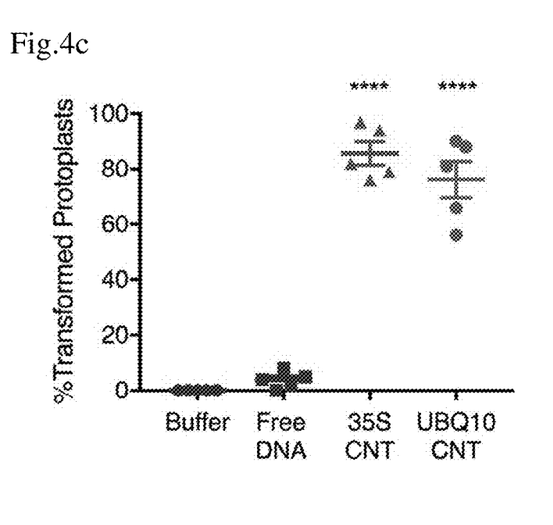
FIG. 4(c) Percentage of the total isolated protoplasts transformed with 35S-CNTs is 86% and with UBQ10-CNT is 76% after a 24-hour incubation period.

We further investigated the ability of CNT nanocarriers to deliver plasmid DNA and trigger functional gene expression in a different plant system—isolated protoplasts, which are cultured plant cells without cell walls. Intact and healthy protoplasts were extracted from arugula leaves through enzymatic cell wall degradation (FIG. 4a) with high efficiency and high yield ($10^7$ total protoplast/10 leaves). The isolated protoplast solution was incubated with plasmid DNA-CNTs, and subsequently imaged with fluorescence microscopy to gauge GFP expression. Additional to the plasmid used in leaf studies, for protoplast experiments we also used a plasmid that encodes a nuclear localization signal (UBQ10-GFP), which transports the expressed GFP from the cytosol into the nucleus. Protoplasts incubated with both types of DNA-CNTs show strong GFP expression correctly localized in cells, whereas protoplasts incubated with free plasmids without CNTs do not show GFP expression (FIG. 4b). Our protoplast transformation efficiencies are 76% and 86% with UBQ10-CNTs and 35S-CNTs, respectively (FIG. 4c).

Figure 5A:
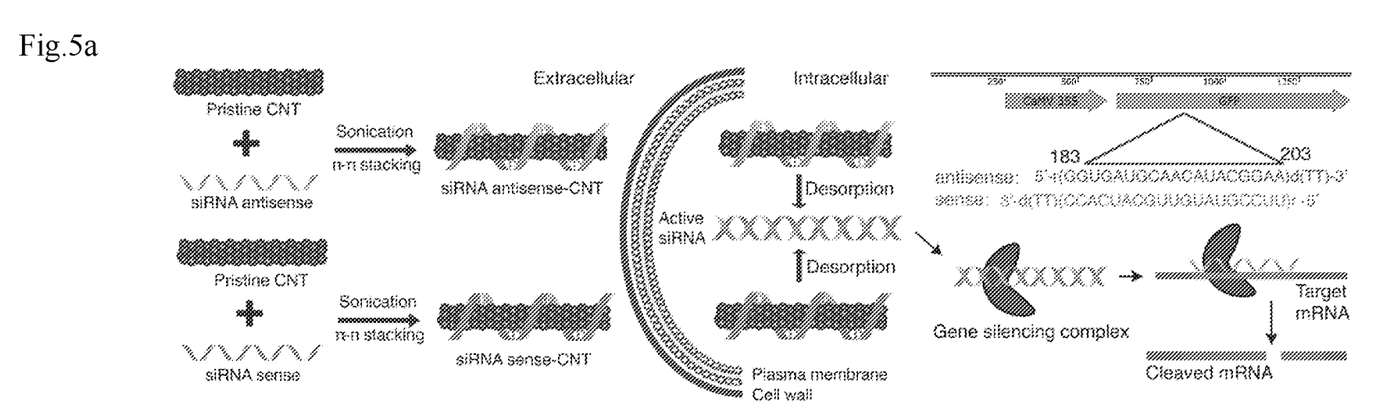
FIG. 5(a). CNT-guided siRNA gene silencing in mature plants; Loading of siRNA on CNTs is accomplished by probe-tip sonication of siRNA sense and antisense sequences with CNTs. Post-infiltration, RNA-CNTs traverse the plant cell wall and membrane, and reach the cytosol. The complementary siRNA strands hybridize to each other and desorb from the CNT surface. The desorbed siRNA activates the gene silencing complex, and acts as a template for complementary mRNA transcript recognition and cleavage.
Figure 5B:
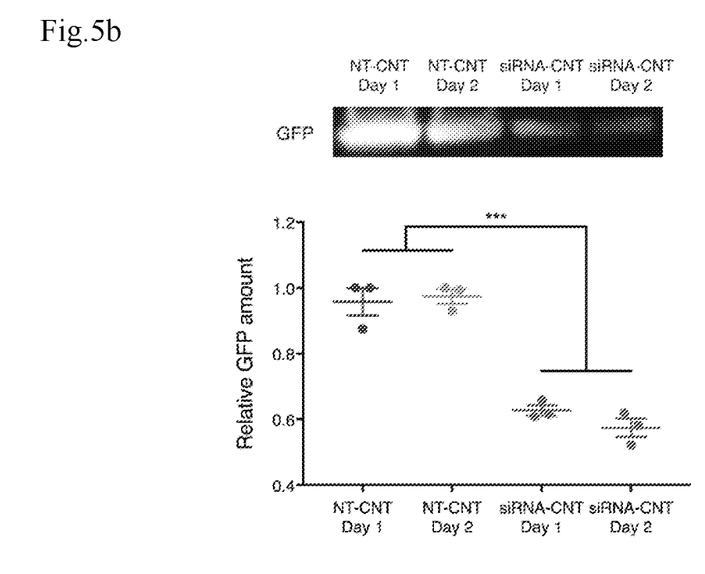
FIG. 5(b) A representative Western blot showing GFP extracted from non-targeting RNA-CNTs (NT-CNT) and siRNA-CNT treated leaves at one and two days post-infiltration. GFP Western blot band intensity analysis shows an average of 43% GFP reduction in siRNA-CNT infiltrated leaves compared to the NT-CNT infiltrated leaves at two-day post-infiltration.
Figure 5C:
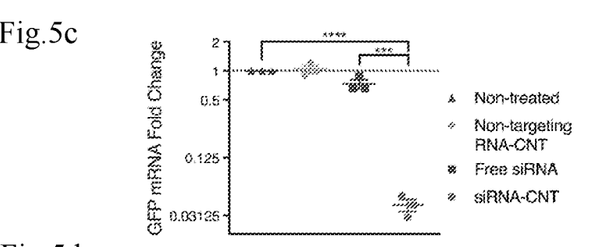
FIG. 5(c) qPCR results show no significant gene silencing in the non-treated leaf, nor in leaves infiltrated with NT-CNT, nor with free GFP-targeting siRNA, whereby 95% gene silencing efficiency is observed when GFP-targeting siRNA is delivered via CNT scaffolding.
Figure 5D:
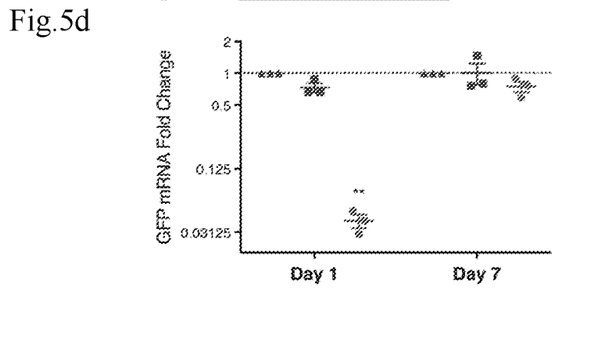
FIG. 5(d) GFP expression nearly returns to its initial value 7-days post-infiltration with siRNA-CNT, suggesting transient gene silencing.

We next demonstrate the applicability of our CNT-mediated delivery tool in plants with another broadly-utilized functional cargo—siRNA. For this study, we silence a gene in transgenic *Nicotiana benthamiana*, which strongly expresses GFP in all cells due to GFP transgene integration in the nuclear genome. To silence this constitutively-expressed GFP gene, we designed a 21-bp siRNA sequence that is specific to the GFP mRNA (FIG. 5a). Loading of siRNA on CNTs is accomplished by probe-tip sonication of each siRNA single-strand (sense and antisense) with SWCNTs. The adsorption of RNA on SWCNTs was confirmed through the emergence of characteristic peaks in the SWCNT near-infrared fluorescence emission spectra for both siRNA sense and antisense suspensions. The mixture of siRNA sense and antisense loaded CNTs was infiltrated into the leaves of mature transgenic *Nicotiana benthamiana* plants. *Nicotiana benthamiana* leaves were imaged via confocal microscopy to monitor GFP silencing at the protein level. Untreated leaves show strong GFP expression, as expected, due to the constitutive expression of GFP in the transgenic plant. Conversely, leaves infiltrated with siRNA-CNTs show reduced GFP fluorescence via confocal microscopy, suggesting effective siRNA-CNT mediated gene silencing. Moreover, Western blot analysis reveals 43% reduction in GFP extracted from siRNA-CNT treated leaves compared to the leaves treated with non-targeting RNA loaded CNTs (NT-CNT) at two days post-infiltration (FIG. 5b). To corroborate our confocal imaging and Western blot results, we performed qPCR analysis of the siRNA-CNT infiltrated plant leaf tissue to quantify silencing at the mRNA transcript level. No significant gene silencing is observed in the non-treated leaf, nor in leaves infiltrated with non-targeting RNA-CNTs, nor in leaves infiltrated with free GFP-targeting siRNA (FIG. 5c), whereby 95% reduction in GFP mRNA is observed when GFP-targeting siRNA is delivered via CNT scaffolding. 7-days following the introduction of siRNA-CNTs, GFP expression as measured by qPCR returns to baseline levels as observed in non-treated leaves (FIG. 5d).

Figure 7A:
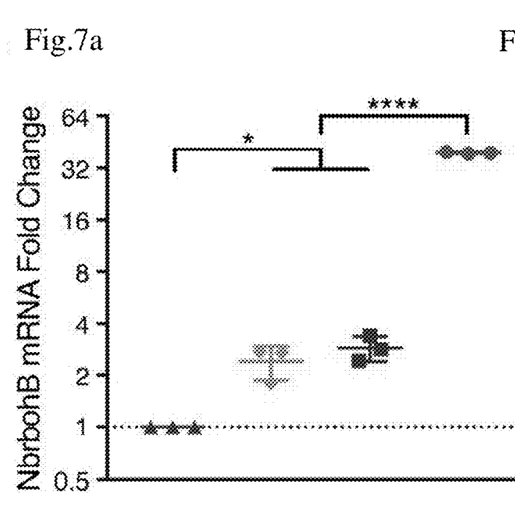
FIG. 7(a). Plant toxicity analyses for DNA-CNTs; qPCR analysis of respiratory burst oxidase homolog B (NbrbohB), a known stress gene in *benthamiana* plants, shows that CNT-treated leaves do not show different NbrbohB expression compared to leaves treated only by infiltration with buffer (0.1 M NaCl). Positive control to induce plant stress for NbrbohB qPCR (10% SDS) shows 40-fold upregulation of NbrbohB.
Figure 7B:
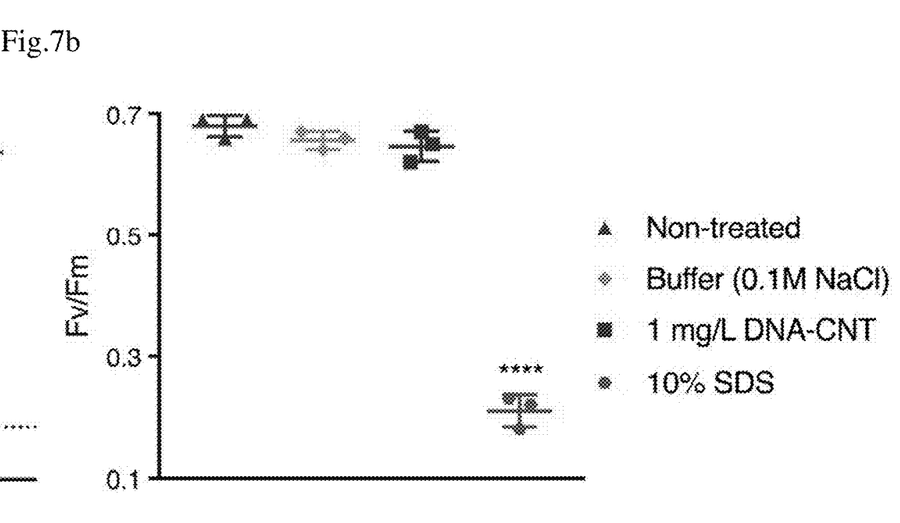
FIG. 7(b) Quantum yield measurements of photosystem II show that CNT-infiltrated leaves show similar photosynthesis quantum yield as control leaves without CNT infiltration. Positive control to induce plant stress for photosystem II quantum yield measurements (10% SDS) shows 68% decrease in photosystem II quantum yield in *benthamiana*.

To test toxicity of CNTs to plant tissue, we performed qPCR analysis of respiratory burst oxidase homolog B (NbrbohB) upregulation (FIG. 7), a known stress gene in *Nicotiana benthamiana* plants. Quantification of NbrbohB expression shows that CNT-treated areas in leaves do not upregulate NbrbohB compared to adjacent areas within the same leaves treated only with buffer. Additionally, quantum yield measurements of photosystem II show that CNT-infiltrated areas in the *benthamiana* leaves have similar photosynthesis quantum yields as control areas within the same leaves without CNT infiltration. Positive controls to induce plant stress for both NbrbohB qPCR and photosystem II quantum yield measurements show clear upregulation of NbrbohB and significant decrease in photosystem II quantum yield in *Nicotiana benthamiana*. Our analysis concludes that the CNT-based delivery platform does not induce any toxicity to mature plants at the concentrations used in this study.

REFERENCES

1. Gozde S. Demirer, Markita P. Landry, Delivering Genes to Plants, SBE Special Section, Plant Synthetic Biology, CEP Magazine, April 2017
2. Cunningham F. J., Goh N. S., Demirer G. S., Matos J., Landry M. P. Nanoparticle-mediated delivery in plants towards advancing plant genetic engineering, in print at *Trends in Biotechnology* (2018).
3. Giraldo, J. P. et al. Plant nanobionics approach to augment photosynthesis and biochemical sensing. Nat Mater 13, 400-408, doi:10.1038/nmat3890
4. Wong, M. H. et al. Lipid Exchange Envelope Penetration (LEEP) of Nanoparticles for Plant Engineering: A Universal Localization Mechanism. Nano Letters 16, 1161-1172, doi:10.1021/acs.nanolett.5b04467 (2016).

The invention claimed is:

1. A method of transiently transforming a plant, comprising: adsorbing sense and anti-sense siRNAs onto pristine single-walled carbon nanotube (CNTs) by probe-tip sonication to form a mixture of siRNA sense and antisense loaded CNTs, wherein the siRNAs comprise a sequence specific for a targeted mRNA; infiltrating a solution of the mixture into leaves of mature *Nicotiana benthamiana* plants using a syringe from the under-side of the leaves, wherein the siRNA sense and antisense loaded CNTs diffuse and penetrate through the full profile of the leaves, then traverse cell walls and membranes to enter cytosol of cells of the leaves, where the sense and anti-sense siRNAs desorb from the siRNA sense and antisense loaded CNTs and transiently silence the targeted mRNA; and detecting a resultant reduced expression of the targeted mRNA, wherein the expression returns to baseline (pre-infiltration level) by day 7 post-infiltration.

2. The method of claim 1, wherein reduced expression comprises a 95% reduction in targeted mRNA compared to pre-infiltration, as measured by quantitative PCR.

* * * * *